United States Patent
Kuyava et al.

(10) Patent No.: US 8,109,870 B2
(45) Date of Patent: Feb. 7, 2012

(54) INFLATABLE PENILE PROSTHESIS BYPASS VALVE NOISE REDUCTION

(75) Inventors: Charles C. Kuyava, Eden Prairie, MN (US); Gregory J. Henkel, Chanhassen, MN (US)

(73) Assignee: AMS Research Corporation, Minnetonka, MN (US)

( * ) Notice: Subject to any disclaimer, the term of this patent is extended or adjusted under 35 U.S.C. 154(b) by 1121 days.

(21) Appl. No.: 11/938,433

(22) Filed: Nov. 12, 2007

(65) Prior Publication Data

US 2008/0114202 A1    May 15, 2008

Related U.S. Application Data

(60) Provisional application No. 60/865,325, filed on Nov. 10, 2006.

(51) Int. Cl.
*A61F 5/00* (2006.01)

(52) U.S. Cl. ........................................................ 600/40

(58) Field of Classification Search ............. 600/29–32, 600/38–41; 623/11.11, 23.67; 128/843; 251/129.15, 30.01, 213, 226, 227, 336, 337; 137/861, 864, 877–882
See application file for complete search history.

(56) References Cited

U.S. PATENT DOCUMENTS

| | | | |
|---|---|---|---|
| 988,120 A * | 3/1911 | Lott | |
| 1,863,057 A * | 6/1932 | Innes | |
| 2,586,575 A * | 2/1952 | Arthur | |
| 2,786,718 A * | 3/1957 | Middlestadt | |
| 3,228,731 A * | 1/1966 | Valentine | |
| 3,312,215 A * | 4/1967 | Silber | |
| 3,344,791 A * | 10/1967 | Foderick | |
| 3,397,699 A * | 8/1968 | Kohl | |
| 3,503,400 A * | 3/1970 | Osthagen et al. | |
| 3,510,029 A * | 5/1970 | Doyle | |
| 3,642,004 A * | 2/1972 | Osthagen et al. | |
| 3,731,670 A * | 5/1973 | Loe | |
| 3,797,478 A * | 3/1974 | Walsh et al. | |
| 3,812,841 A * | 5/1974 | Isaacson | |
| 3,853,122 A * | 12/1974 | Strauch et al. | |
| 3,954,102 A * | 5/1976 | Buuck | |

(Continued)

FOREIGN PATENT DOCUMENTS

DE         2537506 A1 *  8/1975

(Continued)

OTHER PUBLICATIONS

Abouassaly, R. et al, "Antibiotic-coated medical devices: with an emphasis on inflatable penile prosthesis", Asian J Androl. Sep. 2004; 6: 249-57.

(Continued)

*Primary Examiner* — John Lacyk
(74) *Attorney, Agent, or Firm* — Kimberly K. Baxter; Gregory L. Koeller

(57) ABSTRACT

An inflatable penile prosthesis includes an implantable pump having a bypass valve. The bypass valve includes a cavity having a valve seat at a port, a poppet and a spring. The poppet includes a valve member and a stem extending from the valve member. In operation, the poppet includes a sealing position, where the valve member seals the port through contact with the valve seat, and a deflating position, where the valve member is displaced from the valve seat. The spring is configured to bias the valve member toward the valve seat, wherein the spring engages a portion of the stem while the poppet is in the deflating position.

21 Claims, 6 Drawing Sheets

U.S. PATENT DOCUMENTS

| | | | |
|---|---|---|---|
| 4,009,711 A * | 3/1977 | Uson | |
| 4,201,202 A * | 5/1980 | Finney et al. | |
| 4,204,530 A * | 5/1980 | Finney | |
| 4,222,377 A | 9/1980 | Burton | |
| 4,224,934 A | 9/1980 | Scott et al. | |
| 4,235,227 A | 11/1980 | Yamanaka | |
| 4,256,093 A | 3/1981 | Helms et al. | |
| 4,267,829 A | 5/1981 | Burton et al. | |
| 4,318,396 A | 3/1982 | Finney | |
| 4,342,308 A | 8/1982 | Trick | |
| 4,344,434 A | 8/1982 | Robertson | |
| 4,353,360 A | 10/1982 | Finney et al. | |
| 4,360,010 A | 11/1982 | Finney | |
| 4,364,379 A | 12/1982 | Finney | |
| 4,369,771 A | 1/1983 | Trick | |
| 4,378,792 A | 4/1983 | Finney | |
| 4,383,525 A | 5/1983 | Scott et al. | |
| 4,399,811 A | 8/1983 | Finney et al. | |
| 4,399,812 A | 8/1983 | Whitehead | |
| 4,404,968 A | 9/1983 | Evans, Sr. | |
| 4,407,278 A | 10/1983 | Burton et al. | |
| 4,412,530 A | 11/1983 | Burton | |
| 4,424,807 A | 1/1984 | Evans, Sr. | |
| 4,437,457 A | 3/1984 | Trick et al. | |
| 4,441,491 A | 4/1984 | Evans, Sr. | |
| 4,449,520 A | 5/1984 | Palomar | |
| 4,453,536 A | 6/1984 | Abild | |
| 4,457,335 A | 7/1984 | Trick | |
| 4,489,732 A | 12/1984 | Hasson | |
| 4,523,584 A | 6/1985 | Yachia et al. | |
| 4,532,920 A | 8/1985 | Finney | |
| 4,537,183 A | 8/1985 | Fogarty | |
| 4,550,719 A | 11/1985 | Finney et al. | |
| 4,550,720 A | 11/1985 | Trick | |
| 4,553,959 A | 11/1985 | Hickey et al. | |
| 4,558,693 A | 12/1985 | Lash et al. | |
| 4,559,931 A | 12/1985 | Fischell | |
| 4,566,446 A | 1/1986 | Fogarty | |
| 4,571,241 A | 2/1986 | Christopher | |
| 4,572,168 A | 2/1986 | Fischell | |
| 4,574,792 A | 3/1986 | Trick | |
| 4,587,954 A | 5/1986 | Haber | |
| 4,590,927 A | 5/1986 | Porter et al. | |
| 4,596,242 A | 6/1986 | Fischell | |
| 4,602,625 A | 7/1986 | Yachia et al. | |
| 4,604,994 A | 8/1986 | Sealfon | |
| 4,611,584 A | 9/1986 | Finney | |
| 4,622,958 A | 11/1986 | Finney | |
| 4,632,435 A | 12/1986 | Polyak | |
| 4,651,721 A | 3/1987 | Mikulich et al. | |
| 4,653,485 A | 3/1987 | Fischell | |
| 4,664,100 A | 5/1987 | Rudloff | |
| 4,665,903 A | 5/1987 | Whitehead | |
| 4,671,261 A | 6/1987 | Fischell | |
| 4,682,583 A | 7/1987 | Burton et al. | |
| 4,682,589 A | 7/1987 | Finney | |
| 4,710,169 A | 12/1987 | Christopher | |
| 4,718,410 A | 1/1988 | Hakky | |
| 4,724,830 A | 2/1988 | Fischell | |
| 4,726,360 A | 2/1988 | Trick et al. | |
| 4,730,607 A | 3/1988 | Fischell | |
| 4,766,889 A | 8/1988 | Trick et al. | |
| 4,773,403 A | 9/1988 | Daly | |
| 4,782,826 A | 11/1988 | Fogarty | |
| 4,790,298 A | 12/1988 | Trick | |
| 4,791,917 A | 12/1988 | Finney | |
| 4,807,608 A | 2/1989 | Levius | |
| 4,829,990 A | 5/1989 | Thuroff et al. | |
| 4,829,991 A | 5/1989 | Boeck | |
| 4,850,963 A | 7/1989 | Sparks et al. | |
| 4,881,530 A | 11/1989 | Frick | |
| 4,895,139 A | 1/1990 | Hauschild et al. | |
| 4,917,110 A | 4/1990 | Trick | |
| 4,932,938 A | 6/1990 | Goldberg et al. | |
| 4,944,732 A | 7/1990 | Russo | |
| 4,958,630 A | 9/1990 | Rosenbluth et al. | |
| 4,968,294 A | 11/1990 | Salama | |
| 4,988,357 A | 1/1991 | Koss | |
| 5,010,882 A | 4/1991 | Polyak et al. | |
| 5,030,199 A | 7/1991 | Barwick et al. | |
| 5,034,009 A | 7/1991 | Mouchel | |
| 5,041,092 A | 8/1991 | Barwick | |
| 5,048,510 A | 9/1991 | Hauschild et al. | |
| 5,048,511 A | 9/1991 | Rosenbluth et al. | |
| 5,052,383 A | 10/1991 | Chabert | |
| 5,062,416 A | 11/1991 | Stucks | |
| 5,062,417 A | 11/1991 | Cowen | |
| 5,063,914 A | 11/1991 | Cowen | |
| 5,067,485 A | 11/1991 | Cowen | |
| 5,074,849 A | 12/1991 | Sachse | |
| 5,085,650 A | 2/1992 | Giglio | |
| 5,088,980 A | 2/1992 | Leighton | |
| 5,090,424 A | 2/1992 | Simon et al. | |
| 5,101,813 A | 4/1992 | Trick | |
| 5,112,295 A | 5/1992 | Zinner et al. | |
| 5,114,398 A | 5/1992 | Trick et al. | |
| 5,129,880 A | 7/1992 | Grundei | |
| 5,131,906 A | 7/1992 | Chen | |
| 5,141,509 A | 8/1992 | Burton et al. | |
| 5,158,111 A | 10/1992 | Lambert et al. | |
| 5,167,611 A | 12/1992 | Cowan | |
| 5,171,272 A | 12/1992 | Levius | |
| 5,186,180 A | 2/1993 | Bellas | |
| 5,250,020 A | 10/1993 | Bley | |
| 5,263,981 A | 11/1993 | Polyak et al. | |
| 5,328,293 A | 7/1994 | Keefe | |
| 5,344,388 A | 9/1994 | Maxwell et al. | |
| 5,433,694 A | 7/1995 | Lim | |
| 5,518,499 A | 5/1996 | Agar | |
| 5,595,331 A | 1/1997 | Leistner | |
| 5,678,768 A | 10/1997 | Gager et al. | |
| 5,704,895 A | 1/1998 | Scott et al. | |
| 5,851,176 A | 12/1998 | Willard | |
| 5,893,826 A | 4/1999 | Slama | |
| 5,895,424 A | 4/1999 | Steele, Sr. et al. | |
| 6,171,233 B1 | 1/2001 | Willard | |
| 6,443,887 B1 | 9/2002 | Derus et al. | |
| 6,533,719 B2 | 3/2003 | Kuyava et al. | |
| 6,558,315 B1 | 5/2003 | Kuyava | |
| 6,723,042 B2 | 4/2004 | Almli et al. | |
| 6,730,017 B2 | 5/2004 | Henkel et al. | |
| 6,733,527 B2 | 5/2004 | Koyfman | |
| 6,929,599 B2 | 8/2005 | Westrum | |
| 6,935,847 B2 | 8/2005 | Kuyava et al. | |
| 6,991,601 B2 | 1/2006 | Kuyava et al. | |
| 7,066,877 B2 | 6/2006 | Kuyava | |
| 7,066,878 B2 | 6/2006 | Eid | |
| 7,169,103 B2 | 1/2007 | Ling et al. | |
| 7,244,227 B2 | 7/2007 | Morningstar | |
| 7,250,026 B2 | 7/2007 | Kuyava | |
| 2002/0033564 A1 | 3/2002 | Koyfman | |
| 2002/0082473 A1 | 6/2002 | Henkel et al. | |
| 2002/0082709 A1 | 6/2002 | Almli et al. | |
| 2002/0091302 A1 | 7/2002 | Kuyava et al. | |
| 2003/0028076 A1 | 2/2003 | Kuyava et al. | |
| 2004/0193005 A1 | 9/2004 | Almli | |
| 2004/0220447 A1 | 11/2004 | Morningstar | |
| 2004/0220448 A1 | 11/2004 | Henkel | |
| 2005/0250982 A1 | 11/2005 | Kuyava | |
| 2006/0135845 A1 | 6/2006 | Kuyava | |

FOREIGN PATENT DOCUMENTS

| | | | |
|---|---|---|---|
| EP | 0051420 | * | 5/1982 |
| EP | 0065853 | * | 12/1982 |
| EP | 0682923 | * | 11/1995 |
| EP | 0925764 | * | 6/1999 |
| GB | 2160777 | * | 1/1986 |
| GB | 2192546 | | 1/1988 |
| WO | WO8000302 | | 3/1980 |
| WO | WO8500513 | | 2/1985 |
| WO | WO9203107 | | 3/1992 |
| WO | WO9404095 | | 3/1994 |
| WO | WO02051339 | | 7/2002 |

OTHER PUBLICATIONS

Agrawal, V. et al. "An audit of implanted penile prostheses in the UK", BJU International 98, 293-295 (2006).

Akin-Olugbade, O. et al, "Determinants of Patient Satisfaction Following Penile Prosthesis Surgery", J Sex Med 2006; 3: 743-48.
Al-Najar, A., et al, "Should being aged over 70 years hinder penile prosthesis implantation?", BJU International 2009 1-4.
AMS 700 CX Penile Prosthesis (Brochure) 2 pages 1999.
AMS 700 Inflatable Penile Prosthesis Product Line 45 pages (1992).
AMS (Brochure) 700 Series Tactiel (Pump 2 pages) 2004.
AMS (Brochure) Ultrex/Ultrex Plus (10 Pages)(1998).
AMS Ambicor Penile Prosthesis (Brochure) 1996.
Merino, G. Atienza, "Penile Prosthesis for the treatment of erectile dysfunction" Actas Urol Esp. 2006; 30(2): 159-69.
Candela, J. et al "Three-piece inflatable penile prosthesis implantatoin: . . . " J La State Med Soc 148:296-301 (1996).
Daitch, J. et al, "Long-Term Mechanical Reliability of AMS 700 Series Inflatable Penile Prostheses: Comparison . . . " J. Urol. 158: 1400-1402; Oct. 1997.
Delk, J. "Early Experience with the American Medical Systems New Tactile Pump: Results of a Multicenter Study" J Sex med 2005; 2: 266-271.
Deuk Choi, Y. et al. "Mechanical Reliability of the AMS 700CXM Inflatable Penile Prosthesis for the Treatment of Male Erectile Dysfunction" J. Urol 168, 822-824, Mar. 2001.
Deveci, S. et al "Penile Length Alterations following Penile Prosthesis Surgery" Europan Urol. 51 (2007) 1128-31.
Gefen, A. "Stresses in the normal and diabetic human penis following implantation of an inflatable prosthesis." Med. Biol. Eng. Comput., 1999, 37, 625-31.
Garber, B. "Inflatable penile prostheses for the treatment of erectile dysfunction." Exper Rev. Med. Devices 2(3), 341-50 (2005).
Gefen, A Et Al. "A biomechanical model of Peyronie's disease" J. Biomech.33 (2000) 1739-44.
Gefen, A Et Al. "Optimization of Design and Surgical Positioning of Inflatable Penile Prostheses" Annals of Biomed. Eng. 28 (2000) 619-28.
Henry, G "Advances in Penile Prosthesis Design", Current Sexual Health Reports 2007, 4:15-19.
InhibiZone Antibiotic Surface Treatment, (AMS Brochure) 4pgs 2001.
Kadioglu, A. et al. "Surgical Treatment of Peyronie's Disease: A Critical Analysis" european urology 50 ( 2006 ) 235-248.
"Kava, B et al ""Efficacy and Patient Satisfaction Associated with Penile ProsthesisRevision Surgery"" J Sex Med 2007;4:509-518".
Lazarou, S., et al, "Technical Advances in Penile Prostheses" J Long-Term Effects of Med. Imp. 16 (3):235-247(2006).
Levine, L et al, "Mechanical Reliability and Safety of, and Patient Satisfaction With the Ambicor Inflatable Penile Prosthesis: . . . " J Urol vol. 166, 932-937, Sep. 2001.
Lumen, N. "Phalloplasty: A Valuable Treatment for Males with Penile Insufficiency", Urology 71 (2), 2008 272-276.
Lux, M. et al. "Outcomes and Satisfaction Rates for the Redesigned 2-Piece Penile Prosthesis" J Urol. vol. 177, 262-266, Jan. 2007.
Mentor New from Mentor Urology Alpha I Narrow-Base (Brochure) 2pgs 1996.
Mentor Alpha I Inflatable Penile Prosthesis (Brochure) 2 pgs Jul. 1996.
Mentor Surgical Protocol Alpha I Inflatable Penile Prosthesis 17pgs May 1998.
Mentor Patient Guide for Alpha I Inflatable Penile Implant (Brochure) 2pgs 1997.
Montague, D., "Penile Prosthesis Implantation for End-Stage Erectile Dysfunction After Radical Prostatectomy" Reviews in Urol. vol. 7 Suppl. 2 2005 S51-S57.
Mulcahy, J. "Distal Corporoplasty for Lateral Extrusion of Penile Prosthesis Cylinders" J. Urol. vol. 161, 193-195 Jan. 1999.
Murphy, Am., Et al. "Failure of the Ambicors inflatable penile prosthesis to deflate" International Journal of Impotence Research (2005) 17, 291-292.
"Parylene Micro Coating" AMS Brochure, 4 pgs 2000.
Sadeghi-Nejad, H. "Penile Prosthesis Surgery: A Review of Prosthetic Devices and Associated Complications" J Sex Med 2007;4:296-309.
Scarzella, Ig,. Et al. "Use of Amibcor Penile Prosthesis in Peyronie's Disease and as Replacement for Malfunctioning AMS 700 Devices", J Sex Med 2004; Suppl. 1.
Ultrex Plus Penile Prosthesis (AMS Advertisement) 1 pg (1992).
Wang, Shyh-Jen, et al "Hardness evaluation of penile prostheses" International Journal of Urology (2006) 13, 569-572.
Mentor Surgical Protocol Alpha I Inflatable Penile Prosthesis 15pgs 1998.
Mentor Urology Products, (Brochure), Mentor, 20 pages (1998).
Hellstrom, WJG, "Three-piece inflatable penile prosthesis components (surgical pearls on, . . . )" International Journal of Impotence Research (2003) 15, Suppl 5, S136-S138.
Kim, Sae-Chui, "Mechanical Reliability of AMS Hydraulic Penile Prostheses" J. of Korean Med. Sci. 10(6); 422-425, Dec. 1995.
Mooreville, M. et al Implantation of Inflatable Penile Prosthesis in Patients With Severe Corporeal Fibrosis: Introduction of a New Penile . . . J. Urol 162, 2054-2057, Dec. 1999.
Montague, DK "Cylinder Sizing: less is more" International Journal of Impotence Research (2003) 15, Suppl 5, S132-S133.
Montague, DK et al, "Penile Prosthesis Infections" International Journal of Impotence Research (2001) 13, 326-328.
Malloy, T., et al.,"Improved Mechanical Survival with Revised Model Inflatable Penile Prosthesis Using Rear-Tip Extenders", J Urol. 128 Sep. 1982 489-491.
Chang, Yao-Jen, et al "Penile Prosthesis Implantation" eMedicine http://www.emedicine.com/med/topic3047.htm 19 pages (2003).
Gregory, J., et al., "The Inflatable Penile Prosthesis: Failure of the Rear Tip Extender in Reducing the Incidence of Cylinder Leakage" J Urol. vol. 131 668-669 (1984).
Joseph, D., et al., "Bilateral Disloctin of Rear Tip Extenders from the Inflatable Penile Prosthesis" J Urol vol. 128, Dec. 1982 1317-1318.

* cited by examiner

INFLATABLE PENILE PROSTHESIS BYPASS VALVE NOISE REDUCTION

CLAIM TO PRIORITY

The present application claims priority to U.S. application No. 60/865,325, filed Nov. 10, 2006 and entitled "Inflatable Penile Prosthesis Bypass Valve Noise Reduction." The identified provisional patent application is hereby incorporated herein in its entirety.

BACKGROUND OF THE INVENTION

One common treatment for male erectile dysfunction is the implantation of a penile prosthesis. An exemplary inflatable penile prosthesis 10 is shown in FIG. 1. Penile prostheses typically include a pair of inflatable cylinders 12, which are fluidly connected to a reservoir 14 via a pump and valve assembly 16 through tubing 18. The two cylinders 12 are normally implanted into the corpus cavernosae of the patient and the reservoir 14 is typically implanted into the patient's abdomen. The pump assembly 16 is implanted in the scrotum. A detailed description of the exemplary penile prosthesis 10 is provided in U.S. Publication No. 2006/0135845, which is hereby incorporated by reference herein.

During use, the patient actuates the pump 16 and fluid is transferred from the reservoir 14 to the pump 16 through tubing 20. The fluid travels through the pump 16 and into the cylinders 12 through tubing 18. This results in the inflation of the cylinders 12 and thereby produces the desired penis rigidity for a normal erection. Then, when the patient desires to deflate the cylinders 12, a valve assembly within the pump 16 is actuated in a manner such that the fluid in the cylinders 12 is released back into the reservoir 14. This deflation then returns the penis to a flaccid state.

The pump and valve assembly 16 includes fluid pathways allowing the flow of fluid to and from the reservoir 14, as well as to and from the cylinders 12. In some designs this fluid flow is controlled by one or more poppet valves positioned in the fluid pathways within the housing of the pump and valve assembly 16.

A compressible pump bulb 22 is typically attached to the housing 24 of the pump assembly 16 and is in fluid communication with the various fluid pathways. In order to inflate the cylinders 12, the compressible pump bulb 22 is actuated by the patient, thereby urging fluid in the bulb 22 past the poppet valves into the cylinders 12. In order to deflate the cylinders 12, the valve housing 24 is grasped and squeezed, such as at button 26, through the patient's tissue, causing the various poppet valves to unseat and allow fluid to flow back to the reservoir 14 through a ball check valve (i.e., bypass valve) contained in the housing 24.

FIG. 2 is simplified illustration of an exemplary bypass valve 30 during cylinder inflation or a steady state condition. The bypass valve 30 includes a poppet 31 in the form of a spherical valve member 32 within a bypass cavity 34. The valve member 32 is biased against a valve seat 36 of an input port 38 of the cavity 34 by a spring 40. The coils of the spring 40 are not shown in the figures in order to simplify the illustrations.

FIG. 3 is a simplified illustration of the bypass valve 30 during cylinder deflation. During deflation of the cylinders 12, the operator releases the seal formed by various poppet valves within the housing 24 to direct a flow of fluid, represented by arrows 42, from the cylinders 12 through the input port 38 of the bypass cavity 34. The pressure of the flow of fluid overcomes the bias force supplied by the spring 40 and displaces the valve member 32 from the valve seat 36. The flow of fluid 42 travels through the bypass cavity 34, through an output port 44 and back to the reservoir 14, as mentioned above.

As the flow of fluid is continuously modulated by the throttling of the valve 30, the ball 32 moves rapidly (vibrates) toward and away from the valve seat 36, as indicated by arrow 46. This vibration induces an audible sound outside of the pump 16. As the velocity of the flow decreases in response to decreasing pressure within the cylinders 12, the frequency of the sound increases, eventually sounding like a high pitched scream (approximately 3000 Hz) toward the end of the deflation operation.

SUMMARY OF THE INVENTION

The present invention generally relates to solutions to the bypass valve noise problem during deflation operations of the inflatable penile prosthesis.

One embodiment of the invention is directed to a bypass valve of an implantable pump of an inflatable penile prosthesis that utilizes frictional resistance to movement of the poppet to reduce noise during deflation operations.

In accordance with another embodiment of the invention, audible noise during deflation operations is decreased by decreasing the frequency at which the spring and poppet system naturally vibrate through an increase in the mass of the poppet and/or a decrease in the spring constant of the spring as compared to bypass valves of the prior art.

These and other features will become apparent with a careful review of the drawings and the corresponding detailed description.

DETAILED DESCRIPTION OF THE PREFERRED EMBODIMENTS

The frequency of a vibrating spring mass system is proportional to $\sqrt{K/M}$, where K=the spring constant and M=the system mass. The bypass valve 30 of FIGS. 2 and 3 form such a spring mass system and the frequency of vibration of the sound generated during cylinder deflation is affected by the spring constant of the spring 40 and the mass of the valve member 32.

Figure 2:
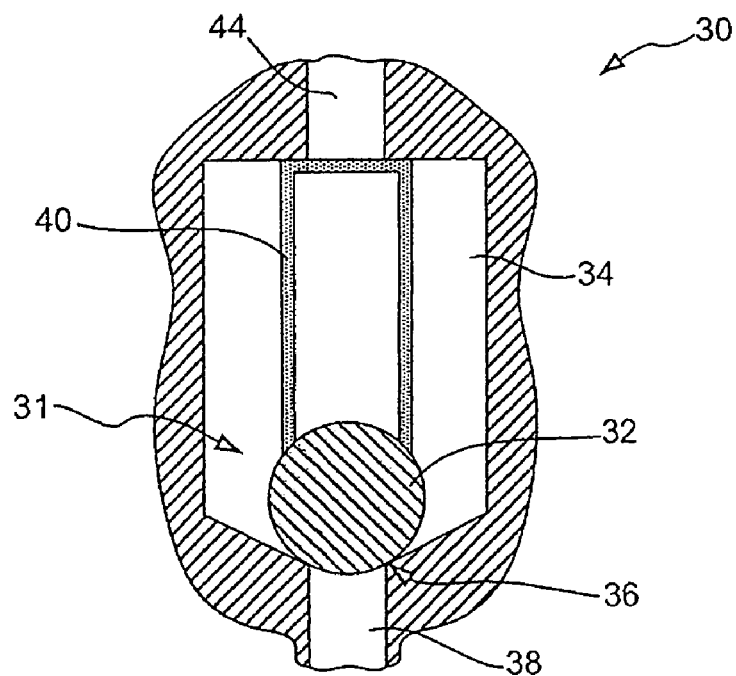
FIG. 2 is a simplified cross-sectional view of a bypass valve during cylinder inflation or a steady state condition.
Figure 3:
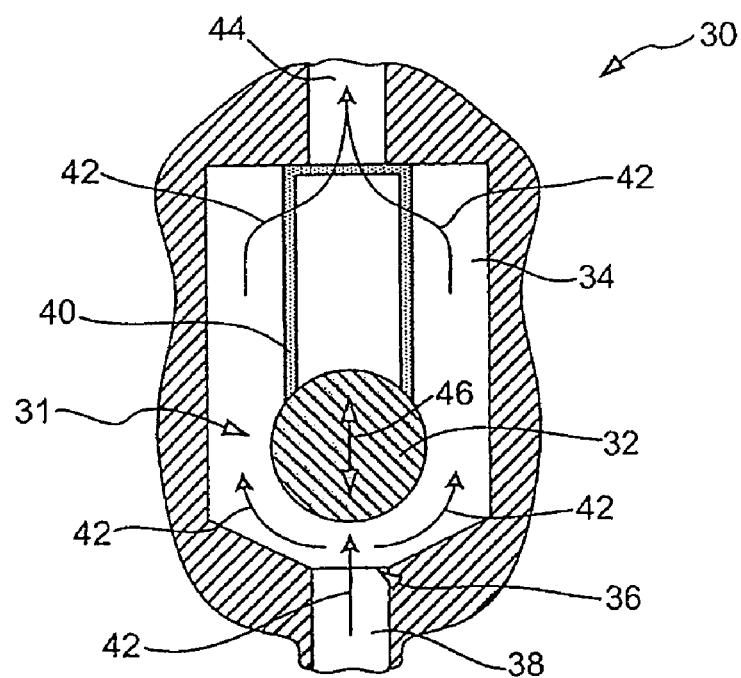
FIG. 3 is a simplified cross-sectional view of a bypass valve during cylinder deflation.

Conventional bypass valves, such as that depicted in FIGS. 2 and 3, utilize a spherical valve member 32 (i.e., a ball) that is formed of synthetic sapphire having a diameter of 3/32 of an inch and a mass of 28 mg. The typical spring 40 of the conventional bypass valve has a spring constant on the order of 80 gm/cm. The resultant frequency of the sound generated during cylinder deflation is in the range of 3000 Hz.

Figure 4:
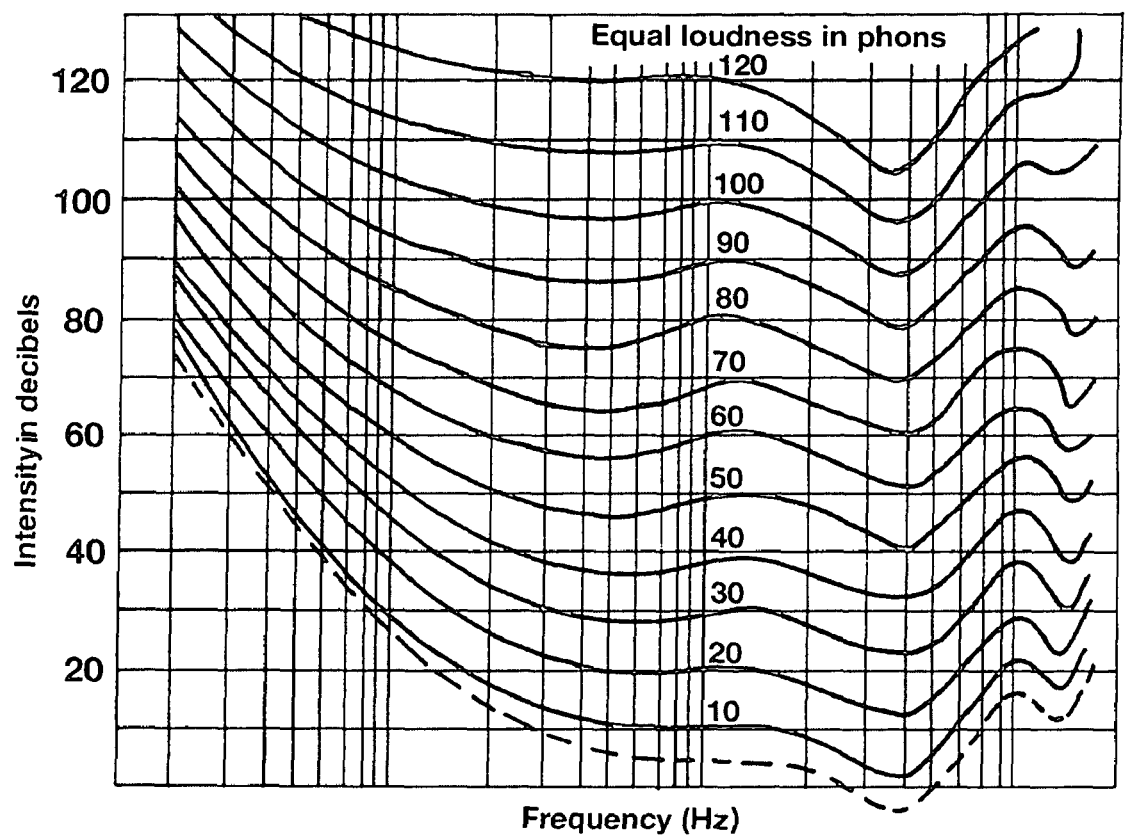
FIG. 4 is a chart containing Robinson-Davidson equal loudness curves adopted by the International Standards Organization as the basis for ISO 266:1987.

While decreasing the spring constant and/or increasing the mass of the ball will decrease the system vibrating frequency, such a change would not affect the actual sound level (i.e., amplitude). However, the human ear perceives the loudness of sound differently at different frequencies. This effect is seen in the Robinson-Davidson equal loudness curves adopted by the International Standards Organization as the basis for ISO 266:1987, shown in FIG. 4. For instance, a sound with a loudness of 10 dB at 3,000 Hz will sound 33% as loud at 1,000 Hz and 10% as loud at 100 Hz, and a 20 dB sound at 3,000 Hz will sound 65% as loud at 1,000 Hz and 36% as loud at 100 Hz.

Since the sound levels generated by conventional bypass valves during deflation of the penile prosthesis cylinders are low and the primary frequencies of the generated sounds are in the range of 3,000 Hz, modifying the spring constant and poppet mass can have a significant affect on the sound frequency and therefore the perceived loudness. Embodiments of the invention are directed to decreasing the system vibrating frequency such that the sound generated during cylinder deflation is perceived as having a lower amplitude than that generated by the conventional bypass valve. This is accomplished by increasing the mass of the poppet 31 and/or decreasing the spring constant of the spring 40.

In accordance with one embodiment, the mass of the poppet 31 is increased relative to the conventional design discussed above through an increase in the size of the valve member 32 (e.g., greater than 3/32 of an inch) of the poppet 31. In one exemplary embodiment the poppet 31 includes a spherical valve member 32 having a diameter of 1/8 of an inch or more. The poppet 31 can take on other non-spherical shapes, such as that described below, that have a larger volume than conventional valve members. Thus, even if the material forming the valve member 32 and the spring 40 are conventional, the larger volume valve member 32 will have greater mass than the conventional design resulting in a reduction to the frequency of vibration of the system and a perceived reduction in the noise level.

In another embodiment, the poppet 31 is formed of a material that is more dense than the synthetic sapphire of conventional poppets 32. For example, the valve member 32 can be formed of stainless steel or other relatively dense material (e.g., titanium carbide) that is not subject to corrosion and is appropriate for human implantation. The increase in the mass of the otherwise conventional poppet 31 and spring 40 system, will result in a decrease in the frequency of vibration of the system and a perceived reduction in the noise level.

In accordance with another embodiment, the spring constant of the spring 40 is decreased to provide a reduction to the frequency of vibration of the poppet 31 and spring 40 system.

Embodiments of the invention include setting the frequency of vibration of the spring 40 and poppet 31 system to less than 2500 Hz through an increase in the density of the poppet 31, an increase in the volume of the poppet 31, and/or a decrease in the spring constant of spring 40. In another embodiment, the frequency of vibration of the spring 40 and poppet 31 system is set to below 1500 Hz using the same techniques.

In accordance with one exemplary embodiment, the frequency of vibration of the spring 40 and poppet 31 system is decreased significantly below the 3000 Hz frequency of the conventional valve member and spring systems by increasing the mass of the poppet 31 to approximately 5 times that of the conventional valve member and by reducing the spring constant of the spring 40 by one-third of that of the conventional spring. In one embodiment, the mass of poppet 31 is increased by forming the valve member 32 out of stainless steel and increasing the diameter of the spherical valve member 32 to 1/8 of an inch. These changes in the mass of the valve member and the spring constant relative to the conventional bypass valve result in a decrease in the frequency of the sound generated during cylinder deflation by approximately 63%. Thus, a conventional bypass valve sound of 10 Db and at a frequency of 3000 Hz that is generated during cylinder deflation can be reduced to 1100 Hz. This reduction in the frequency is perceived by the human ear as a further reduction in loudness by approximately 67%.

In accordance with another embodiment of the invention, vibratory movement of the poppet within the bypass cavity is resisted to thereby reduce noise that is generated during cylinder deflation operations. In general, frictional resistance is applied to the poppet to impede vibratory movement of the poppet relative to the valve seat.

Figure 5:
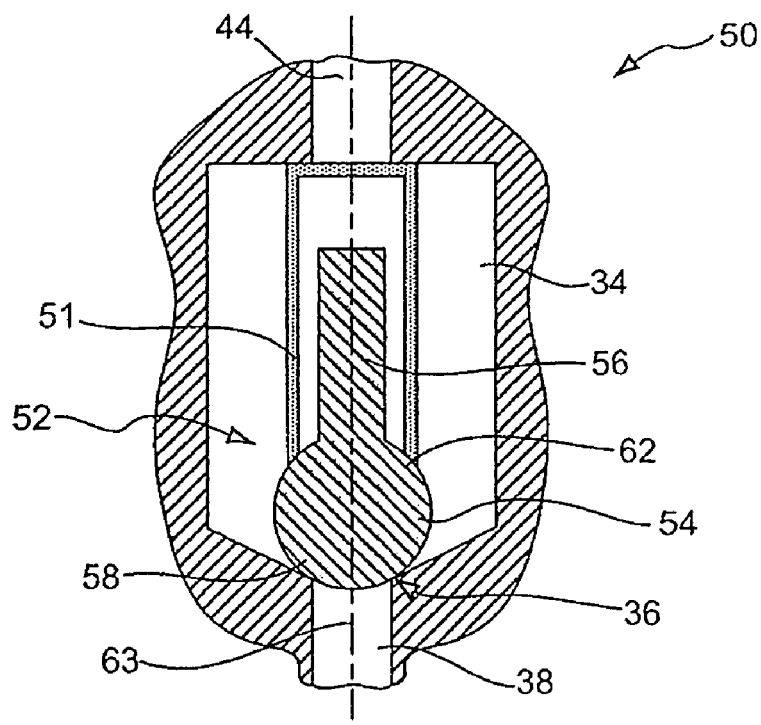
FIG. 5 is a simplified cross-sectional view of a bypass valve of an inflatable penile prosthesis during cylinder inflation or a steady state condition, in accordance with embodiments of the invention.

FIGS. 5-9 are a simplified cross-sectional views of a bypass valve 50 of an inflatable penile prosthesis in accordance with embodiments of the invention. The bypass valve 50 includes a spring 51 and a poppet 52 comprising a valve member 54 and a stem 56 that extends from the valve member 54. The bypass valve 50 also includes some of the conventional elements described above, which are numbered accordingly. The valve member 54 operates as described above to engage the valve seat 36 to seal the input port 38 during inflation and steady state operating conditions, as shown in FIG. 5.

In accordance with one embodiment, the poppet 52 includes a sealing position, shown in FIG. 5, in which a side 58 of the valve member 54 that is opposite the stem 56 engages the valve seat 36 to seal the input port 38. In one embodiment, the side 58 of the valve member 54 has a spherical shape or convex shape, which facilitates the sealing of the circular valve seat 36. The side 58 of the valve member 54 can take on other shapes that conform well to the perimeter of the valve seat 36.

Figure 1:
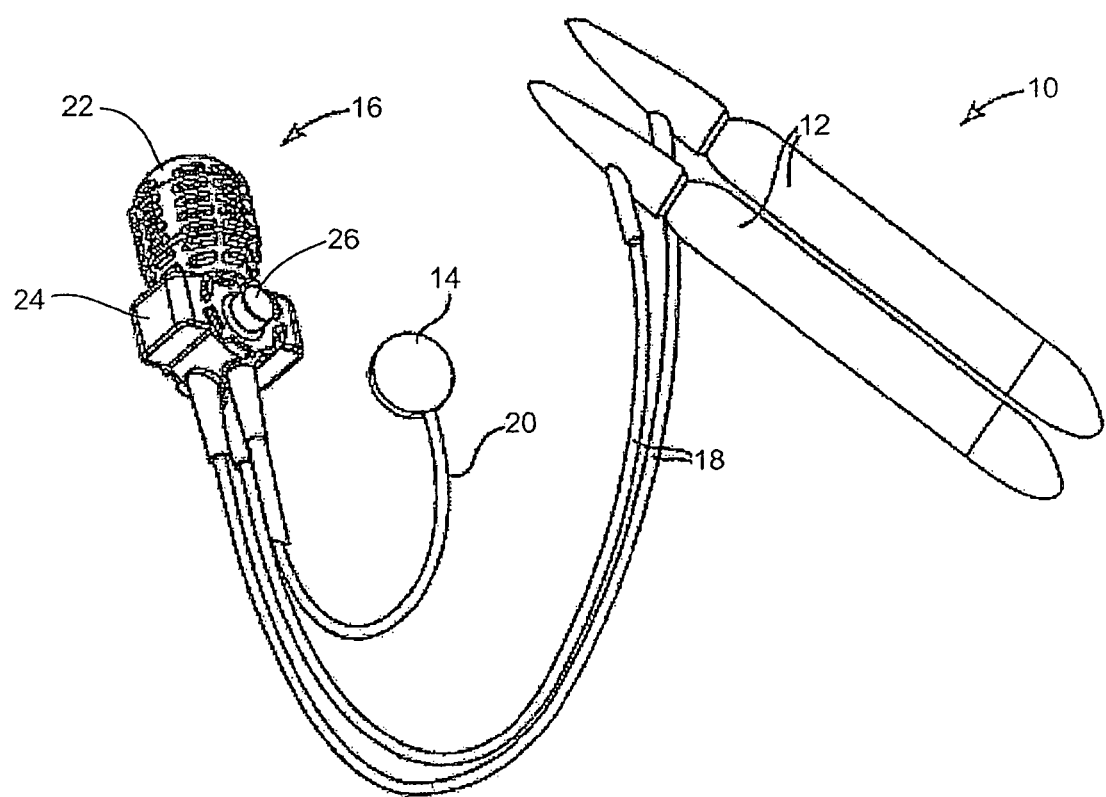
FIG. 1 is an exemplary inflatable penile prosthesis.

The poppet 52 also includes a deflating position, shown in FIGS. 6-9, in which the valve member 54 is displaced from the valve seat 36 thereby opening the input port 38 to a flow of fluid 42 from the cylinders 12 (FIG. 1). During cylinder deflation operations, forces will be applied to the poppet 52 that encourage its vibration toward and away from the valve seat 36, as indicated by arrow 60.

The stem 56 extends from a side 62 of the valve member 54 that is opposite the side 58 designed to seal the valve seat 36. The stem 56 is configured to engage a portion of the spring 51 during cylinder deflation operations. This contact with the spring 51 occurs at a location of the spring 51 where there is relative movement between the spring 51 and the stem 56. As a result, a frictional force is generated at the contact point that resists movement of the poppet 52 relative to the spring 51. This frictional resistance to movement of the poppet 52 dampens the vibratory movement of the poppet 52 during cylinder deflation operations and reduces noise.

The amount of frictional resistance between the poppet 52 and the spring 51 depends on the surfaces of the spring 51 and the stem 56, the contact area, and the pressure applied between the stem 56 and the spring 51. The amount of frictional resistance to movement of the poppet 52 can be set based on empirical testing to provide the desired damping of the vibratory movement of the poppet 52 and noise reduction based on the flow of fluid that is generated during cylinder deflation operations.

In the embodiment illustrated in FIG. 5, the stem 56 of the poppet 52 is received within the cylindrically shaped spring 51. In one embodiment, the stem 56 is sized to allow the poppet 52 to pivot slightly relative to a longitudinal axis 63

Figure 6:
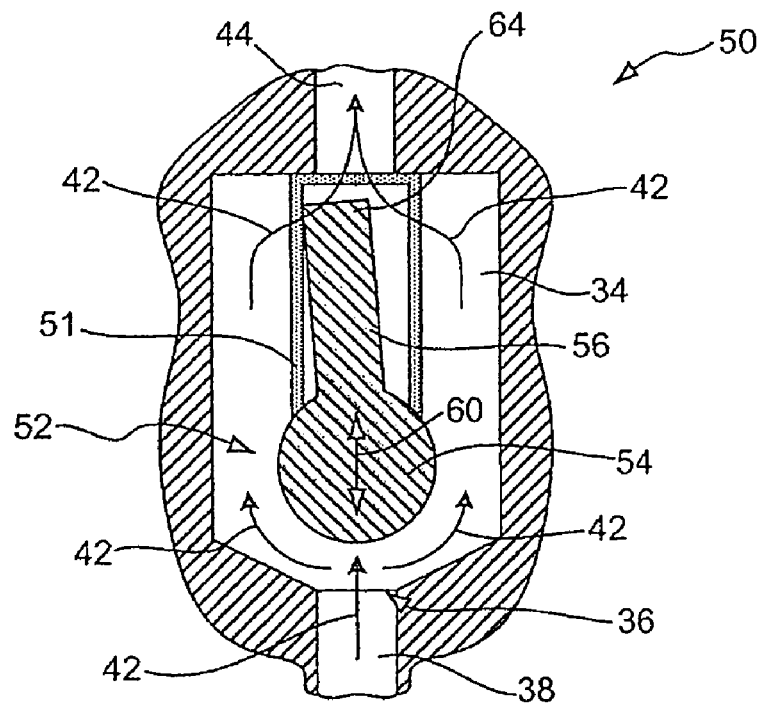
FIG. 6-9 are simplified cross-sectional views of embodiments of a bypass valve during cylinder deflation operations.

(FIG. 5) of the cavity 34 during cylinder deflation operations, such that an end 64 of the stem 56 contacts the spring 51, as shown in FIG. 6. This contact dampens vibratory movement of the poppet 52, as discussed above.

Figure 7:
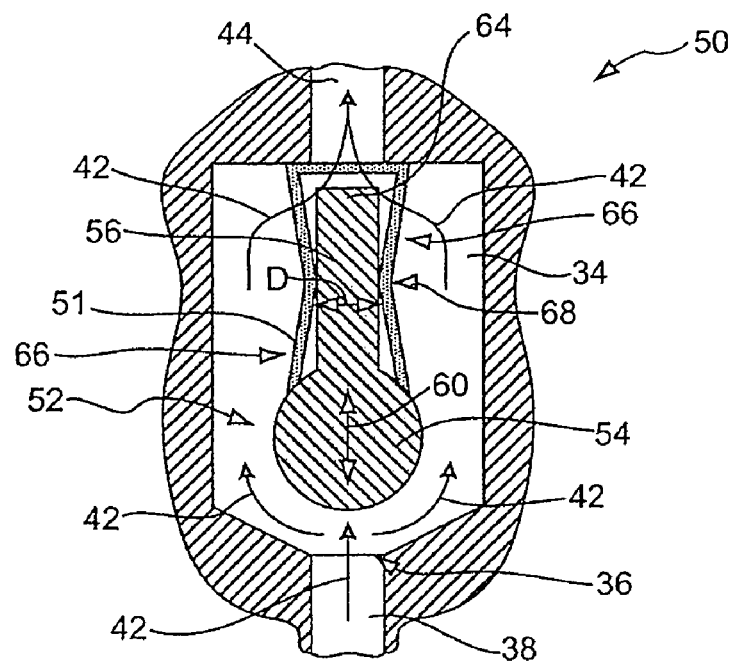

In the embodiment of the bypass valve 50 provided in FIG. 7, the spring 51 has a diameter D that varies along its length. In one embodiment, the spring 51 includes one or more conically shaped sections 66. In another embodiment, the spring 51 has an hourglass shape, as shown in FIG. 7. The variable diameter D of the spring 51 results in at least one constricted portion 68 that contacts the stem 56 and provides the desired frictional resistance to the vibratory motion of the poppet 52.

Figure 8:
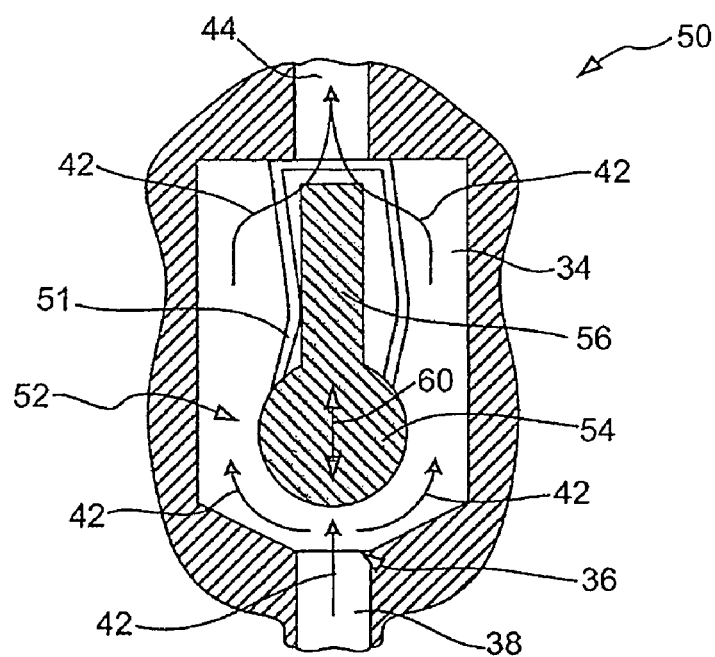

In one embodiment, the spring 51 has a generally cylindrical shape when the poppet 52 is in the sealing position (FIG. 5). However, when the spring 51 is forced to contract during cylinder deflation, the spring 51 buckles into an arced shape resulting in contact with the stem 56, as illustrated in FIG. 8. The contact provides the desired dampening of vibratory motion of the poppet 52.

Figure 9:
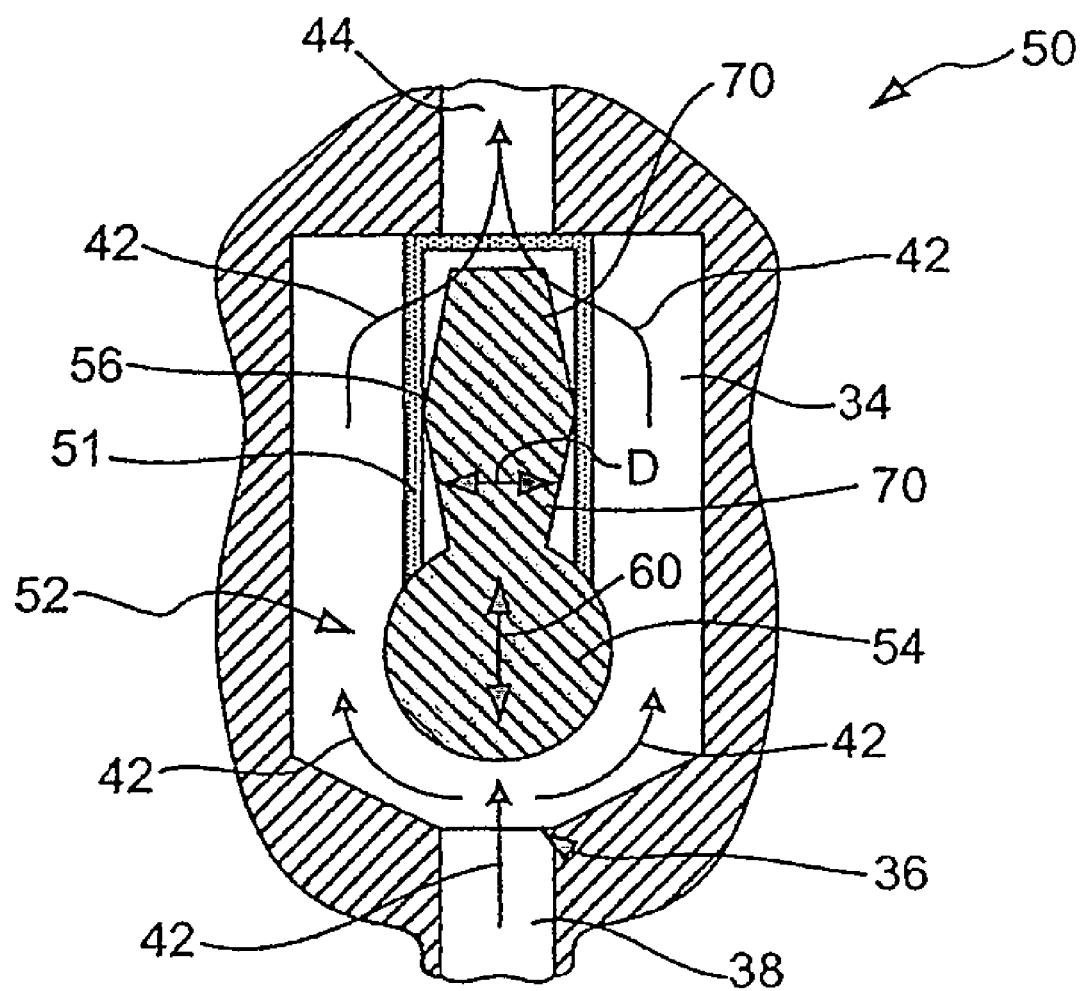

In the embodiment of the bypass valve 50 shown in FIG. 9, the stem 56 has a diameter D that varies along its length. In one embodiment, the stem 56 includes one or more conical sections 70. The variable diameter of the stem 56 results in an expanded section that contacts the spring 51 and provides the desired frictional resistance to the vibratory motion of the poppet 52.

Although the present invention has been described with reference to preferred embodiments, workers skilled in the art will recognize that changes may be made in form and detail without departing from the spirit and scope of the invention.

What is claimed is:

1. A bypass valve of an implantable pump of an inflatable penile prosthesis comprising:
    a bypass cavity having a valve seat at a port;
    a poppet comprising a valve member and a stem extending from the valve member, the poppet including a sealing position, in which the valve member seals the port through contact with the valve seat and a deflating position, in which the valve member is displaced from the valve seat; and
    a spring configured to bias the valve member toward the valve seat, wherein the spring engages a portion of the stem while the poppet is in the deflating position.

2. The valve of claim 1, wherein the stem is cylindrical.

3. The valve of claim 1, wherein the valve member is spherical.

4. The valve of claim 1, wherein the spring is cylindrical.

5. The valve of claim 1, wherein the spring has a diameter that varies along its length.

6. The valve of claim 1, wherein the spring includes a conically shaped section.

7. The valve of claim 1, wherein the stem includes a conically shaped section.

8. The valve of claim 1, wherein the stem has a diameter that varies along its length.

9. The valve of claim 1, wherein the spring engages the stem as the poppet moves between the sealing and deflating positions.

10. The valve of claim 1, wherein the spring is configured to buckle in response to the movement of the poppet from the sealing position to the deflating position.

11. The valve of claim 1, wherein the frequency of the vibrating spring and poppet system is less than 2500 Hz.

12. The valve of claim 1, wherein the frequency of the vibrating spring and poppet system is less than 1500 Hz.

13. An implantable pump of an inflatable penile prosthesis comprising the bypass valve of claim 1.

14. A method of reducing noise produced by a bypass valve of an implantable pump of an inflatable penile prosthesis during deflation of cylinders of the penile prosthesis, the bypass valve comprising a bypass cavity having a valve seat at a port, a poppet comprising a valve member and a stem extending from the valve member, and a spring, the method comprising steps of:
    biasing the poppet with the spring into a sealing position, in which the valve member seals the port through contact with the valve seat;
    introducing a flow of fluid to the port;
    moving the poppet from the sealing position to a deflating position in response to the flow of fluid, wherein the valve member is displaced from the valve seat and the flow of fluid travels through the bypass cavity; and
    inhibiting vibratory movement of the poppet relative to the valve seat through frictional resistance between the stem and the spring.

15. A bypass valve of an implantable pump of an inflatable penile prosthesis:
    a bypass cavity having a valve seat at a port;
    a poppet comprising a valve member, the poppet including a sealing position in which the valve member seals the port through contact with the valve seat and a deflating position, in which the valve member is displaced from the valve seat; and
    a spring biasing the valve member toward the valve seat;
    wherein the frequency of the vibrating spring and poppet system is less than 2500 Hz.

16. The valve of claim 15, wherein the frequency of the vibrating spring and poppet system is less than 1500 Hz.

17. The valve of claim 15, wherein the valve member is formed of stainless steel.

18. The valve of claim 15, wherein the valve member is spherical and has a diameter that is greater than 3/32 of an inch.

19. The valve of claim 18, wherein the diameter of the valve member is greater than or equal to 1/8 of an inch.

20. The valve of claim 15, wherein the spring has a spring constant selected from the group of less than 80 gm/cm, less than 70 gm/cm and less than 60 gm/cm.

21. The valve of claim 15, wherein:
    the poppet further comprises a stem extending from the valve member; and
    the spring engages a portion of the stem while the poppet is in the deflating position.

* * * * *